United States Patent
Masi et al.

(10) Patent No.: US 7,449,528 B2
(45) Date of Patent: Nov. 11, 2008

(54) SUPPORTED CATALYST CONTAINING ACTIVE TITANIUM IN THE HOMO, CO-, AND TER-POLYMERIZATION OF OLEFIN-UNSATURATED COMPOUNDS

(75) Inventors: Francesco Masi, Sant'Angelo Lodigiano-Lodi (IT); Roberto Santi, deceased, late of Novara (IT); by Maria Rivellini, legal representative, Novara (IT); by Stefano Santi, legal representative, Novara (IT); by Laura Santi, legal representative, Novara (IT); Anna Sommazzi, Santa Margherita Ligure (IT); Antonio Proto, Novara (IT); Mario Polesello, Ferrara (IT); Andrea Vallieri, Bologna (IT)

(73) Assignee: Polimeri Europa S.p.A., Brindisi (IT)

( * ) Notice: Subject to any disclaimer, the term of this patent is extended or adjusted under 35 U.S.C. 154(b) by 246 days.

(21) Appl. No.: 10/497,549

(22) PCT Filed: Dec. 6, 2002

(86) PCT No.: PCT/EP02/13954

§ 371 (c)(1),
(2), (4) Date: Apr. 25, 2005

(87) PCT Pub. No.: WO03/054034

PCT Pub. Date: Jul. 3, 2003

(65) Prior Publication Data

US 2006/0014631 A1 Jan. 19, 2006

(30) Foreign Application Priority Data

Dec. 20, 2001 (IT) .......................... MI2001A2710

(51) Int. Cl.
*C08F 4/42* (2006.01)

(52) U.S. Cl. ................. 526/124.2; 526/124.3; 526/351; 526/348.6; 502/103; 502/115; 502/118

(58) Field of Classification Search ................. 526/351, 526/348.6, 124.2, 124.3; 502/103, 115, 118
See application file for complete search history.

(56) References Cited

U.S. PATENT DOCUMENTS 3,875,075 A   4/1975   Boone et al.
6,225,420 B1 *   5/2001   Palmqvist et al. .............. 526/65

FOREIGN PATENT DOCUMENTS

WO   9722633   6/1997

OTHER PUBLICATIONS

Rafikov et al., Izvestiya akademii Nauk SSSR, Seriya Khimicheskaya, No. 7, p. 1615-1617 (1976).*
Rafikov S R et al: "Effect of the chemical nature of the substituent in titanium tetrachlorid derivatives on the Ziegler polymerization of butadiene" Akademiya Nauk SSR Izvestiya. Seriya Khimicheskaya, Moscow, RU, No. 7, 1975, pp. 1615-1617, XP002181172, the whole document.

* cited by examiner

*Primary Examiner*—Ling-Siu Choi
(74) *Attorney, Agent, or Firm*—Oblon, Spivak, McClelland, Maier & Neustadt, P.C.

(57) ABSTRACT

The present invention relates to a supported catalyst containing titanium, its preparation and it use in the homo-, co-, and ter-polymerization of olefin-unsaturated compounds. The present invention also relates to a catalytic system comprising a supported catalyst based on titanium and a co-catalyst selected from organo-derivatives of aluminum. More specifically, the present invention relates to catalyst supported on silica, obtained by reacting a titanium halocarboxylate and a magnesium halocarboxylate with an aluminum chloroakyl-derivative, in the presence of a carrier consisting of high porosity silica. The above reaction essentially takes place in the pores of the silica itself.

24 Claims, No Drawings

SUPPORTED CATALYST CONTAINING ACTIVE TITANIUM IN THE HOMO, CO-, AND TER-POLYMERIZATION OF OLEFIN-UNSATURATED COMPOUNDS

The present invention relates to a supported catalyst containing titanium, active in the preparation of polymer, copolymers and terpolymers, starting from olefin-unsaturated compounds.

The present invention also relates to a catalytic system comprising a supported catalyst containing titanium and a cocatalyst selected from organo-derivatives of aluminum.

More specifically, the present invention relates to a catalyst supported on silica, obtained by reacting one or more titanium halocarboxylates and one or more magnesium halocarboxylates with an aluminum chloroakylderivative, in the presence of a carrier essentially consisting of high porosity silica. The above reaction essentially takes place in the pores of the silica itself.

Heterogeneous catalysts essentially consisting of derivatives of magnesium and titanium supported on inert materials (for example silica or alumina) are known as being active in the polymerization of ethylene, particularly in gas phase. For example, U.S. Pat. No. 4,359,561 describes the preparation of these materials and their use, together with an activator, in the polymerization of ethylene in gas phase. The preparation of these materials has numerous disadvantages. Regardless of the inert carrier, in fact, it is necessary to have (1) at least one titanium compound, (2) at least one magnesium compound, (3) at least one electron donor, (4) at least one boron halide, (5) at least one activator.

Furthermore, the silica, the preferred inert carrier, must be dehydrated by means of treatment at 800° C. (see Example 1 of U.S. Pat. No. 4,379,758).

Finally, high volumes of solvents are required. Example 1 of U.S. Pat. No. 4,379,758 again requires 2.5 liters of purified THF to dissolve, after heating, 41.8 grams of MgCl$_2$ and 27.7 grams of TiCl$_4$. 500 grams of silica impregnated with magnesium and titanium are then suspended in 3 liters of isopentane and treated with a 1 M solution of boron trichloride in methylene chloride.

The copending patent application filed by the same applicant IT MI01A000858 describes the preparation of titanium halocarboxylates, preferably titanium chlorocarboxylates, useful in the homo-, co- and ter-polymerization of alpha-olefins with non-conjugated dienes.

These titanium halocarboxylates are suitable for the preparation of EPR elastomers and EPDM terpolymers. EP(D)M terpolymers in fact have a sufficiently narrow molecular weight distribution (M$_w$/M$_n$<3), are random (r$_e$xr$_p$≦1.0) and are obtained with acceptable productivity (about 13-18 kg/g of titanium).

The catalytic systems based on titanium described in the above patent application IT MI01A000858 have the well-known disadvantages of homogeneous catalytic systems, for example difficulty in producing high molecular weights and unsatisfactory yields. In addition, they are not suitable for the homopolymerization of α-olefins.

A catalyst based on titanium supported on silica has now been found, which overcomes the drawbacks described above, as it can be used for the homo-, co- and ter-polymerization of olefin-unsaturated compounds, with medium to high yields. The catalyst of the present invention also allows high molecular weights to be obtained, when desired.

With respect to U.S. Pat. No. 4,379,758, the preparation of the supported catalyst of the present invention also has the considerable advantage of being very simple and requiring minimum quantities of non-polar solvents. Furthermore, there is no pretreatment step of the silica at high temperatures.

In accordance with this, the present invention relates to a catalyst supported on silica, active in the polymerization, copolymerization and terpolymerization of olefin-unsaturated compounds, the above silica having a surface area of ≧200 m$^2$/g, preferably from 250 to 400 m$^2$/g, a total cumulative pore volume greater than 1 ml/g, preferably from 1.1 to 3 ml/g, even more preferably from 1.2 to 2 ml/g, a quantity of total surface hydroxyls (isolated, vicinal, geminal) of less than 1.0 meq/g, preferably from 0.4 to 0.6 meq/g, an average particle diameter ranging from 5 μm to 100 μm, preferably from 20 μm to 60 μm, a free humidity content lower than or equal to 2% by weight, preferably lower than 1% by weight, obtained by means of a process which comprises:

(i) deposition in the pores of the above silica of at least one solution of (i1) at least one derivative of magnesium selected from bis magnesium halocarboxylates and halogen magnesium halocarboxylates having general formula (II)

$$MgX'_m(R'\text{---}COO)_{(2-m)} \qquad (II)$$

wherein

X' is a halogen, excluding iodine, preferably chlorine;

m is selected from 0 to 1;

R' is a monofunctional hydrocarbyl radical having from 1 to 20 carbon atoms and from 1 to 6 halogen atoms, selected from chlorine and bromine, preferably chlorine;

and of (i2) at least one derivative of titanium selected from titanium halocarboxylates having general formula (I):

$$(RCOO)_n TiX_p \qquad (I)$$

wherein:

p+n=2, 3, 4, preferably=3;

n≧1;

R has the same meaning as R';

X is selected from chlorine, bromine, alkoxyl, carboxyl, beta-dicarbonyl group, preferably chlorine;

and wherein the atomic ratio between the Mg in (II) and Ti in (I) ranges from 0.5/1 to 10/1;

(ii) subsequent deposition, on the silica containing derivatives of magnesium and titanium obtained at the end of step (i), of a solution of one or more halogen alkyl derivatives of aluminum selected from those having general formula (III) AlR''$_n$X''$_{3-n}$ (with n=1 or 2) and (IV) Al$_2$R''$_n$X''$_{6-n}$ (n=1-5) wherein R'' is a C$_1$-C$_{20}$ alkyl group, X'' is chlorine or bromine, preferably chlorine; and wherein the ratio between the sum of the halogen atoms in (III) and/or (IV) and the total carboxyl groups in (I) and (II) varies from 0.3/1 to 10/1, preferably from 0.5/1 to 4.0/1;

(iii) reaction, inside the silica pores containing derivatives of Ti, Mg, Al obtained at the end of step (ii), between the halogen alkyl derivative of aluminum having general formula (III) or (IV) and compounds (I) and (II), thus obtaining a supported catalyst consisting of porous silica containing, inside the pores, derivatives of magnesium, titanium, aluminum and by-products essentially based on aluminum;

(iv) recovery of the supported catalyst obtained at the end of step (iii), after elimination by washing of the aluminum-based by-products.

The R'—COO carboxyl groups in formula (II) and R—COO carboxyl groups of general formula (I) are selected from:

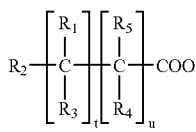

wherein $R_1$, $R_2$, $R_3$, $R_4$ and $R_5$, the same or different, are selected from H, F, Cl, Br, a monofunctional hydrocarbyl radical as such or having at least one of its hydrogen atoms substituted with a halogen selected from chlorine, bromine, fluorine, preferably chlorine; on the condition that at least one of the residues from $R_1$ to $R_5$ is selected from fluorine, chlorine or bromine, preferably chlorine, or a monofunctional hydrocarbyl group containing a halogen selected from fluorine, chlorine or bromine, preferably chlorine; t and u independently vary from 0 to 10.

Non-limiting examples of these derivatives are represented by:
$CCl_3COO$, $CCl_3CH_2COO$, $CCl_3(CH_2)_2COO$, $CHCl_2COO$, $CH_3CCl_2COO$, $C_6H_5CCl_2CH_2COO$, $(C_6H_5)_2CClCOO$, $CH_3CH_2CCl_2COO$, $C_6H_5(CH_2)_3CHClCOO$, $ClC_6H_4CHClCOO$, $ClC_6H_4CH_2COO$, $Cl_2C_6H_3CH_2COO$, 2-cyclopropyl-2,2-dichloro-acetic acid.

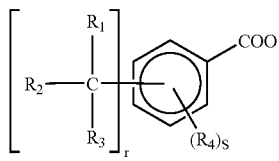

wherein:
$R_1$, $R_2$, $R_3$, $R_4$ have the meaning defined above, on the condition that at least one of the residues from $R_1$ to $R_4$ is selected from fluorine, chlorine or bromine, preferably chlorine, or a monofunctional hydrocarbyl group containing a halogen selected from fluorine, chlorine or bromine, preferably chlorine;
r and s independently vary from 0 to 5, with the constraint that r+s ranges from 1 to 5.

Non-limiting examples of these derivatives are represented by: $Cl_3CC_6H_4COO$, $ClCH_2C_6H_4COO$, $ClCH_2C_6H_2Cl_2COO$, $C_6Cl_5COO$.

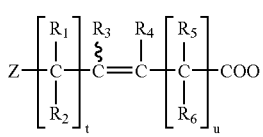

wherein:
$R_1$, $R_2$, $R_3$, $R_4$ and $R_5$ have the meaning defined above, Z, $R_5$, $R_6$ have the same meaning as the other substituents, on the condition that at least one of the residues Z and $R_1$-$R_6$ is selected from fluorine, chlorine or bromine, preferably chlorine, or a monofunctional hydrocarbyl group containing a halogen selected from fluorine, chlorine or bromine, preferably chlorine; t and u independently vary from 0 to 10, preferably from 0 to 2.

Non-limiting examples of these derivatives are represented by:
$CCl_3CH=CHCOO$, $CCl_3CCl=CClCOO$, $CCl_2=CClCCl_2COO$.

4) R—COO wherein R is a monofunctional hydrocarbyl radical selected from cycloalkyl, polycycloalkyl, cycloalkenyl, polycycloalkenyl, having from 3 to 20 carbon atoms, substituted with at least one fluorine, chlorine or bromine, preferably with at least one chlorine, or with hydrocarbyl groups containing at least one fluorine, chlorine or bromine, preferably chlorine.

Non-limiting examples of these derivatives are represented by:
2-chlorocyclohexane-carboxylic acid, 2,2-dichlorocyclopropane-carboxylic acid, 2,2,-3,3-tetra-chlorocyclopropane-carboxylic acid, perchloro-cyclohexane-carboxylic acid, cyclo-hex-2-ene-2-trichloromethyl-carboxylic acid.

The catalyst of the present invention has an atomic composition $Si_{20-70}Mg_{0.5-10}Al_{0.2-1}Ti_1Cl_{5-40}$ and is active in the homopolymerization, copolymerization and terpolymerization of olefin-unsaturated compounds. In particular, the above catalyst is active in the homopolymerization of alpha-olefins, in the copolymerization of ethylene and alpha-olefins, in the copolymerization of ethylene with cyclic olefins, in the terpolymerization of ethylene-alpha-olefins-non-conjugated dienes.

The titanium content of the supported catalyst thus obtained can vary within a wide range. In the preferred embodiment, the above catalyst has a titanium content higher than 0.5% by weight, preferably from 0.6 to 3.0% by weight, even more preferably from 0.6 to 2% by weight, with respect to the total weight of the solid catalyst.

As already mentioned, the molar ratio Mg/Ti of the catalyst of the present invention ranges from 0.5/1 to 10/1. More specifically, for low temperature homo-, co- and ter-polymerization processes ($\leq 100°$ C.), the above ratio preferably ranges from 0.5/1 to 4/1, whereas for high temperature (co) polymerization processes (from 100° C. at 260° C.) said ratio preferably ranges from 5/1 to 8/1.

In a preferred embodiment, step (i) of the process of the present invention can be carried out by the following succession of operations: (ia) preparation of a hydrocarbon solution of compounds (I) and (II); (ib) treatment of the silica with a volume of the solution of (I) and (II) from 15% to 50%, preferably from 20% to 45%, higher than the total cumulative pore volume of the silica, the above treatment being prolonged until the almost complete deposition of compounds (I) and (II) in the silica pores; (ic) elimination, preferably at reduced pressure, of the solvent used to dissolve compounds (I) and (II). Step (i) is preferably carried out at room temperature, or at a temperature ranging from 20 to 30° C., in the presence of means suitable for stirring the mixture of silica and solution of (I)+(II). It can be effected by adding the silica to the solution of (I) and (II), or vice versa. At the end of step (ic), or after the elimination of the solvent, a silica is obtained in whose pores magnesium or titanium derivatives are deposited.

In a preferred embodiment, step (ii) can be carried out using the same procedure described for step (i) after dissolution of the halogen alkyl derivative of aluminum (III) and/or (IV) in a suitable inert solvent. Also in this case the silica is treated with a volume of solution from 15% to 50%, preferably from 20% to 35%, higher than the total cumulative pore volume of the silica.

In a preferred embodiment, step (iii) is carried out by heating the silica obtained at the end of step (ii) to a temperature ranging from 30° C. to 120° C., preferably from 40° C. to 100° C.

Step (iv) consists in washing the silica obtained at the end of step (iii) and in the subsequent recovery of the supported catalyst thus obtained. Preferred solvents for the washing are $C_5$-$C_7$ aliphatic hydrocarbons. In the preferred embodiment the catalyst thus obtained is dried after washing at reduced pressure at a temperature lower than 40° C.

The catalyst thus obtained at the end of the process of the present invention is free-flowing. Furthermore, it has average particle dimensions almost equivalent to the starting values of the silica.

The solvent used for dissolving the magnesium and titanium derivatives in step (i) and the halogen alkyl derivatives of aluminum in step (ii), can be any organic solvent inert (non-reactive) towards the substances dissolved therein. Aliphatic, cycloaliphatic or aromatic hydrocarbon solvents, liquid under the operating conditions, are preferred for the purpose, for example hexane, heptane, octane, nonane, decane, undecane, dodecane, cyclopentane, cyclohexane, benzene, toluene, xylenes and mesitylenes. Aromatic solvents, particularly toluene, are preferred.

The process of the present invention has the great advantage of requiring much lower quantities of solvent with respect to the processes of the prior art.

The compounds having general formula (II) can be prepared with a simple and convenient method. More specifically, the compounds having general formula (II) can be obtained by the reaction of a halocarboxylic acid R'—COOH (wherein R' has the meaning defined above) with a magnesium halide $MgX_2$ (wherein X has the meaning defined above), according to the reaction:

$$MgX_2 + (2-m)R'\text{—COOH} \rightarrow MgX_m(R'\text{—COO})_{(2-m)} + (2-m)HX$$

wherein m is selected from zero and 1.

The magnesium halide used for the purpose is preferably selected from magnesium halides with a particle-size preferably not higher than about 100 μm and with preferably less than 1% by weight of water. The reaction between the magnesium halide and halocarboxylic acid R'—COOH is conveniently carried out in an inert organic solvent, preferably an aliphatic or cycloaliphatic or aromatic solvent, eliminating the hydrogen halide which is developed as reaction by-product, for example by bubbling a stream of inert gas.

At the end of the reaction, a solution of halomagnesium halocarboxylate or magnesium bis halocarboxylate is obtained in dissolved form in the solvent used as reaction medium. The solvent is obviously selected so as to have the maximum solubility possible of the reagents and reaction products. For example, paraffinic solvents are preferred when aliphatic R'—COOH acids are used, and aromatic solvents when aromatic or prevalently aromatic R'—COOH acids are used. The use of mixed solvents is obviously not excluded. In any case, any possible non-dissolved materials can be separated by filtration or decanting. In the preparation of compounds (II), it is convenient to operate with a concentration of $MgX_2$ ranging from 0.1 to 0.7 M, as with higher values there is a lowering in the yield of compound (II) desired.

When, in the compound having general formula (II), "m" is equal to zero, as an alternative to common inorganic magnesium salts, organic magnesium derivatives such as magnesium dialkyls and magnesium monochloro monoalkyls (Grignard), can be used (but they are not economically convenient).

Examples of these preparations are provided in the experimental part.

Finally, it is also possible to use MgO or $MgCO_3$, provided that the humidity content is lower than 1% by weight.

As far as the titanium complexes having general formula (I) are concerned, these are described in the copending patent application filed by the same applicant MI 2001 A000858, which also describes the preparation.

The complexes having general formula (I) can be prepared according to any of the following processes. The first process comprises the following steps:

(a) treatment of a thallium salt having the general formula RCOOTl, wherein R has the meaning defined above, with a titanium compound having the general formula $TiY_nX_s$, wherein (r+s=2, 3, 4); s≧1; X is selected from chlorine, bromine, iodine, preferably chlorine; Y, the same or different from X, is a group of an anionic nature bound to Ti as anion in an ionic couple or with a covalent bond of the "σ" type, said treatment being carried out in a hydro-carbyl solvent or in a chlorinated solvent, preferably heptane or toluene;

(b) separation, preferably filtration, of the thallium halide formed in step (a), (c) isolation of the titanium complex having general formula (I).

Typical but non-limiting examples of $TiY_nX_s$ compounds are titanium halides, such as $TiCl_4$, $TiCl_3$, $TiCl_2(AcAc)_2$.

In the preferred embodiment, step (c) is carried out by evaporation of the solvent or precipitation of the complex following the addition of a suitable precipitant, usually a hydrocarbon solvent, preferably pentane.

Step (a) is preferably carried out at a temperature ranging from C to 50° C., even more preferably from 15 to 30° C. At this temperature, the duration of step (a) indicatively ranges from 30 minutes to 6 hours. Reaction times of 1 to 4 hours are generally sufficient.

The second process comprises:

(a') Direct reaction between a titanium compound having the general formula $TiY_nK_s$ with one or, more carboxylic acids having the general formula RCOOH in an aliphatic or aromatic hydrocarbon solvent or in a chlorinated solvent, preferably heptane or toluene, until the stoichiometric development of hydrochloric acid.

(b') Isolation of the titanium complex having general formula (I) formed in step (a').

In the preferred embodiment, step (b') is carried out by evaporation of the solvent or precipitation of the complex following the addition of a suitable precipitant, usually a hydrocarbon solvent, preferably pentane. Step (a') is preferably carried out at a temperature ranging from 0 to 200° C., even more preferably from 15 to 120° C. At these temperatures the duration of step (a') indicatively ranges from 30 minutes to 48 hours. Reaction times ranging from 1 to 16 hours are normally sufficient.

Typical but non-limiting examples of these syntheses are provided in the experimental part.

Typical but non-limiting examples of RCOO in the compound having general formula (I) are $CCl_3COO$, $CCl_3CH_2COO$, $CCl_3(CH_2)_2COO$, $CHCl_2COO$, $CH_3CCl_2COO$, $C_6H_5CCl_2CH_2COO$, $(C_6H_5)_2CClCOO$, $CH_3CH_2CCl_2COO$, $C_6H_5(CH_2)_3CHClCOO$, $ClC_6H_4CHClCOO$, $2,4\text{-}Cl_2C_6H_3CH_2COO$, $ClC_6H_4CH_2COO$, 2-cyclopropyl-2,2-dichloro-acetate, $Cl_3CC_6H_4COO$, $ClCH_2C_6H_4COO$, $ClCH_2C_6H_2Cl_2COO$, $C_6Cl_5COO$, $CCl_3CH=CHCOO$, $CCl_3CCl=CClCOO$, $CCl_2CClCCl_2COO$, 2-chlorocyclohexane-carboxylate, 2,2-dichlorocyclopropane-carboxylate, 2,2,3,3-tetrachlorocyclopropane-carboxylate, per-chlorocyclohexane-carboxylate, cyclo-hex-2-ene-2-trichloro-methyl-carboxylate.

As far as the halogen alkyl derivatives of aluminum are concerned, typical examples of compounds having general formula (III) are AlEt$_2$Cl (diethylaluminum chloride), AlMe$_2$Cl (dimethylaluminum chloride), AlEtCl$_2$ (ethylaluminumdichloride), Al(i-Bu)$_2$Cl (diisobutylaluminum chloride), Al(i-Bu)Cl$_2$ (isobutylaluminumdichloride); typical examples of compounds having general formula (IV) are Al$_2$Et$_3$Cl$_3$ (ethylaluminum sesquichloride), Al$_2$Me$_3$Cl$_3$ (methylaluminum sesquichloride).

A further object of the present invention relates to a catalytic system for the homo-, co- and ter-polymerization of olefin-unsaturated compounds which comprises:

(a) catalyst supported on silica, prepared as described in claim 1, having an atomic composition:

$$Si_{20-70}Mg_{0.5-10}Al_{0.2-1}Ti_1Cl_{5-40}$$

(b) organo aluminum derivatives selected from aluminoxanes and compounds having general formula (V) AlR$_3$ wherein R is a C$_1$-C$_{20}$ alkyl group.

The molar ratio between the organo aluminum derivatives (b) and titanium contained in the supported catalyst (a) ranges from 5/1 to 2000/1, preferably from 10/1 to 1000/1, more preferably from 20/1 to 800/1.

Typical examples of compounds having general formula (V) are AlMe$_3$ (trimethylaluminum), AlEt$_3$ (triethylaluminum), Al(i-Bu)$_3$ (triisobutylaluminum), Al(n-oct)$_3$ (trioctylaluminum).

As far as the aluminoxanes are concerned, it is known that these are compounds containing Al—O—Al bonds, with a varying O/Al ratio, obtained by the reaction, under controlled conditions, of an aluminum alkyl, or aluminum alkyl halide, with water or other compounds containing pre-established quantities of available water, as, for example, in the case of the reaction of aluminum trimethyl with aluminum hexahydrate sulfate, copper pentahydrate sulfate or iron pentahydrate sulfate. Aluminoxanes preferably used for the formation of the polymerization catalyst of the present invention are cyclic and/or linear, oligo- or polymeric compounds, pounds, characterized by the presence of repetitive Units having the following formula:

$$-\!\!\left(\mathrm{Al}\!-\!\mathrm{O}\right)\!\!-$$
$$\quad\;\;|\;\;$$
$$\quad\;\;R_{15}$$

wherein R$_{15}$ is a C$_1$-C$_6$ alkyl group, preferably methyl. Each aluminoxane molecule preferably contains from 4 to 70 repetitive units which may also not all be the same, but contain different R$_{15}$ groups.

The catalysts of the present invention can be substantially used in all known homo-, co- and ter-polymerization processes of olefin-unsaturated compounds. In particular, the catalysts of the present invention are used in the homo- and co-polymerization of α-olefins having from 3 to 10 carbon atoms, for example propylene, 1-butene, 1-hexene, 1-octene, 4-methyl-1-pentene, and cyclic olefins, for example, norbornene. The above processes can be carried out in suspension, at low pressure (up to about 20 bars), or at medium pressure (from about 20 to about 100 bars), at temperatures ranging from 30 to 100° C.; or in a solution in an inert diluent at pressures ranging from 10 to 150 bars and temperatures ranging from 120 to 260° C.; or in gas phase, with temperatures generally within the range of 60 to 100° C., at pressures ranging from 5 to 50 bars. The polymers or copolymers thus obtained can have a wide molecular weight range. If the molecular weight is to be regulated to a lower value than the maximum value obtainable, it is possible to use a chain transfer agent such as, for example, hydrogen, according to what is known in the art.

The catalysts of the present invention can also be used in the copolymerization of ethylene with alpha-olefins, particularly propylene, and with cyclic olefins, and in the terpolymerization of ethylene with alpha-olefins and non-conjugated dienes. Elastomeric ethylene-propylene copolymers and ethylene-propylene-non-conjugated diene terpolymers to give EPDM rubbers, are particular interesting.

The non-conjugated diene can be selected from:
alicyclic dienes with a linear chain such as 1,4-hexadiene and 1,6-octadiene;
acyclic dienes with a branched chain such as 5-methyl-1,4-hexadiene, 7-methyl-1,6-octadiene, 3,7-dimethyl-1,6-octadiene, 3,7-dimethyl-1,7-octadiene;
alicyclic dienes with a single ring such as 1,4-cyclohexadiene, 1,5-cyclo-octadiene;
dienes having condensed and bridged alicyclic rings such as methyltetrahydroindene, 5-ethylidene-2-norbornene (ENB), 5-propenyl-2-norbornene.

In the preferred embodiment, the diene is selected from ENB and 7-methyl-1,6-octadiene.

The elastomeric EP(D)M copolymers which can be obtained with the catalysts of the present invention usually contain from 10 to 98% in moles of propylene and quantities not higher than 5% of ENB.

Finally, the catalyst of the present invention can be used in the preparation of ethylene-cyclic olefin copolymers, particularly ethylene-norbornene.

When operating with a process in which the polymer which is formed is insoluble in the reaction medium, it repeats the morphology of the catalyst obtaining particles of free-flowing polymer with an average diameter from 5 to 20 times greater than that of the silica used for the preparation of the catalyst.

The following examples are provided for a better understanding of the present invention.

EXAMPLES

Characterization of the Silicas

The characteristics of the carrier (surface area and pore volume) were determined by means of BET whereas the quantity of —OH by means of IR and volumetric gas titration. The BET analysis was carried out using a SORPTOMATIC apparatus mod. 1900 Fisons. The IR analysis was effected on samples of tablets treated at 160° C. under vacuum using an FTIR Perkin-Elmer 1800 spectrophotometer. The volumetric gas titration was carried out with aluminum trimethyl using diglyme as solvent. The particle diameter was determined by means of granulometric analysis using a Malvern Particle Size 2600 instrument.

The residual humidity content was determined with a Karl Fisher Metrohom titrator model 684 KF Coulometer.

Characterization of the Supported Catalysts and Carboxylates having General Formula (I) and (II)

The characterization by means of $^1$H-NMR spectroscopy was effected on a Bruker MSL-300 spectrometer.

The characterization by means of FT-IR spectroscopy was effected on a Perkin-Elmer 1800 FT-IR spectrometer with 4 cm$^{-1}$ resolution and 64 scans.

The titanium and magnesium determination was effected on an inductively coupled plasma spectrometer (ICP) with atomic emission detection (AES) Perkin Elmer Plasma II.

The determination of the silicon and total chlorine was carried out by means of a Philips PW 1404/10 sequential X-ray fluorescence spectrometer (XRF) with an Sc/Mo double anode tube.

The total chlorine is given by the sum of inorganic chlorine (i.e. bound to titanium) and organic chlorine (i.e. chlorine bound to a hydrocarbyl residue).

The measurement was carried out on alcohol solutions of the titanium complex diluted with Milliq water at 2% by weight of $HNO_3$ with a ratio of 1:100 for the determination of the titanium and 1:1 for that of the chlorine. The concentrations centrations of titanium and chlorine were calculated on the basis of a calibration curve obtained with solutions with a known titer of the element to be determined (Ti or Cl) and having an identical composition to that of the samples (water, EtOH, $HNO_3$).

The determination of inorganic Cl was effected potentiometrically using a Titroprocessor 670 and an Ag electrode (cod. 6.0404.000) filled with a saturated solution of $KNO_3$ (both Metrohm). The alcohol solution of the sample was acidified with $H_2SO_4$ 3 M and titrated with $AgNO_3$ 0.1 N.

Characterization of the Polymers

The molecular weight measurement was carried out by means of Gel-permeation chromatography (GPC). The analyses of the samples were effected in 1,2,4-trichlorobenzene (stabilized with N,N'-m-phenylenedimaleimide) at 135° C. with a WATERS 150-CV chromatograph using a Waters differential refractometer as detector. The chromatographic separation was obtained with a set of µ-Styragel HT columns (Waters) with pore dimensions of $10^3$, $10^4$, $10^5$ Å, and $10^6$ Å, establishing a flow-rate of the eluant of 1 ml/min. The data values were acquired and processed by means of Maxima 820 software version 3.30 (Millipores). The calibration curve used for calculating the number average molecular weight (Mn) and weight average molecular weight (Mw) was obtained using polystyrene standard samples with molecular weights within the range of 6,500,000-2,000, and applying the Mark-Houwink equation valid for linear polyethylene and polypropylene; the molecular weight values were corrected in relation to the composition of the polymer using the Scholte equation.

The propylene content in the ethylene-propylene co-polymers and ethylene-propylene-diene terpolymers was determined on samples in the form of film using an FT-IR Perkin Elmer 1800 spectrometer with 4 $cm^{-1}$ resolution and 64 scans, measuring the band absorptions at 4390 and 4255 $cm^{-1}$, on the basis of the calibrations curves set up with copolymers having a known composition.

The microstructure of the polymers ($r_E x r_P$, reactivity ratio of the monomers, and m/r, meso/raceme configuration ratio for the propylene units) was determined by means of $^{13}C$-NMR spectroscopy on a Bruker AM 300 instrument. The spectra of the polymers were registered in $C_2D_2Cl_4$: $C_2H_2Cl_4$ (1:1 mixture by volume) at 100° C. The central peak of $C_2D_2Cl_4$ at 74.52 ppm was used as reference. The delay between one scanning and the subsequent one is 2 seconds and the impulse is equal to 8 µs (about 60°). About 30000 scannings were acquired for each sample. The reactivity ratio $r_E x r_P$ was determined according to the method described in J. C. Carman, H. A. Harrington and C. E. Wilkes, Macromolecules 10, 536 (1977); the m/r ratio was obtained by examining the region of signals relating to the methylene carbons Sαδ and Sαγ, according to the method described in H. N. Cheng, Macromolecules 17, 1950 (1984).

The $T_g$ (glass transition temperature) was determined by means of differential scan calorimetry with a Perkin-Elmer DSC-7.

*** Synthesis of the Compounds Having General Formula (II)

Example 1a

Synthesis of $Mg(OCOCCl_3)_2$ Starting from MgO 408 grams (2.5 moles) of anhydrous trichloroacetic acid are added to a suspension of 40 grams (1 mole) of MgO in 100 ml of heptane. The mixture obtained is heated to reflux temperature and the water formed as by-product is removed by azeotropic distillation. At the end of the reaction, the mixture is cooled and filtered. The solid obtained is washed with pentane until the disappearance of the excess trichloroacetic acid and then dried at 30° C. and $10^{-3}$ mmHg.

331 grams of $Mg(OCOCCl_3)_2$ are thus obtained (95% yield).

Elemental analysis (%): Experimental: Mg 6.91; Cl 61 Theoretical: Mg 6.96; Cl 60.94 IR analysis v ($cm^{-1}$) (nujol) 1670, 1398

Example 1b

Synthesis of $Mg(OCOCCl_3)_2$ Starting from $MgBu_2$ 327 grams (2 moles) of anhydrous trichloroacetic acid are slowly added to 1 liter of $MgBu_2$ (1M in heptane, Aldrich). A white solid precipitates, which is filtered and washed with pentane (6×100 ml), and then dried at 30° C. and $10^{-3}$ mmHg for 8 hours. 345 grams of $Mg(OCOCCl_3)_2$ are thus obtained (99% yield).

Elemental analysis (%): Experimental: Mg 6.80; Cl 61.5 Theoretical: Mg 6.96; Cl 60.94 IR analysis v ($cm^{-1}$) (nujol) 1670, 1398

Example 1c

Synthesis of $Mg(OCOCCl_3)_2$ Starting from $MgCl_2$

In this example and in the following examples, a commercial magnesium chloride is used (residual humidity lower than 1% by weight) consisting of particles having a diameter ranging from 20 to 100 µm.

408 grams (2.5 moles) of anhydrous trichloroacetic acid are slowly added to a suspension of 95 grams (1 mole) of anhydrous $MgCl_2$ in 1000 ml of hexane, maintained at 90° C. The reaction mixture is kept at a constant temperature until the complete development of hydrochloric acid. The mixture is then cooled, filtered, the solid residue is washed with pentane until the disappearance of the excess trichloroacetic acid and is then dried at 30° C. and $10^{-3}$ mmHg for 8 hours.

332 grams of $Mg(OCOCCl_3)_2$ are thus obtained (95% yield).

Elemental analysis (%): Experimental: Mg 7.02; Cl 61.7 Theoretical: Mg 6.96; Cl 60.94 IR analysis v ($cm^{-1}$) (nujol) 1670, 1398

Example 1d

Synthesis of $MgCl(OCOCCl_3)$ Starting from $MgCl_2$ 163.2 grams (1 mole) of anhydrous trichloroacetic acid are slowly added to a suspension of 95 grams (1 mole) of anhydrous $MgCl_2$ in 1000 ml of hexane, maintained at 90° C. The reaction mixture is kept at a constant temperature until the complete development of hydrochloric acid. The mixture is then cooled, filtered, the solid residue is washed with pentane and is then dried at 30° C. and $10^{-3}$ mmHg for 8 hours.

200 grams of MgCl(OCOCCl$_3$) are thus obtained (90% yield).

Elemental analysis (%): Experimental: Mg 11.02; Cl 64.03 Theoretical: Mg 10.94; Cl 63.84 IR analysis v (cm$^{-1}$) (nujol) 1668, 1396

Example 2a

Synthesis of magnesium-bis-(4,4,4-trichlorobutanoate)

403 g (2.1 moles) of 4,4,4-trichlorobutanoic acid are added to 95.2 g (1 mole) of MgCl$_2$ suspended in 2 liters of heptane. The suspension is brought to reflux temperature under a light stream of nitrogen and is maintained at boiling point until the complete development of HCl (8-12 hours). After cooling, the reaction mixture is treated with 10.1 g (0.1 moles) of triethylamine and filtered. 390 g (96% yield) of product are obtained from the filtrate, after evaporation and subsequent drying (30° C., 10$^{-3}$ mmHg, 8 hours), as a white solid with the following elemental analysis:

Elemental analysis (%): Experimental: Mg 5.98; Cl 52.3 Theoretical: Mg 6.00; Cl 52.5 IR analysis v (cm$^{-1}$) (nujol) 1594, 1410

Example 2b

Synthesis of magnesium-bis-(4,4,4-trichloro-but-2-enoate)

397.63 grams (2.1 moles) of 4,4,4-trichlorobut-2-enoic acid are added to 95.2 grams (1 mole) of MgCl$_2$ suspended in 2 liters of heptane. The suspension is brought to reflux temperature under a light stream of nitrogen and is maintained at boiling point, until the complete development of HCl (8-12 hours). After cooling, the reaction mixture is treated with 10.1 g (0.1 moles) of triethylamine and filtered. 380 g (95% yield) of white solid are obtained from the filtrate, after evaporation and subsequent drying, with the following elemental analysis:

Elemental analysis (%): Experimental: Mg 5.98; Cl 54.0 Theoretical: Mg 6.06; Cl 53.03 IR analysis v (cm$^-$) (nujol) 1584, 1420

Example 2c

Synthesis of magnesium-monochloride-(2,4-dichloro-phenylacetate)

215 grams (1.05 moles) of 2,4-dichloro-phenylacetic acid are added to 95.2 grams (1 mole) of MgCl$_2$ suspended in 2 liters of heptane. The suspension is brought to reflux temperature under a light stream of nitrogen and is maintained at boiling point until the complete development of HCl (8-12 hours). After cooling, the reaction mixture is treated with 10.1 g (0.1 moles) of triethylamine and filtered. 253.2 g (96% yield) of white solid are obtained from the filtrate, after evaporation and subsequent drying, with the following elemental analysis:

Elemental analysis (%): Experimental: Mg 9.06; Cl 40.8 Theoretical: Mg 9.21; Cl 40.32 IR analysis v (cm$^-$) (nujol) 1580, 1420

Example 2d

Synthesis of magnesium-monochloride-(4,4,4-trichloro-butanoate) MgCl (OCOCH$_2$CH$_2$CCl$_3$).

202 g (1.05 moles) of 4,4,4-trichloro-butanoic acid are added to 95.2 g (1 mole) of MgCl$_2$ suspended in 2 liters of heptane. The suspension is brought to reflux temperature under a light stream of nitrogen and is maintained at boiling point until the complete development of HCl (8-12 hours). After cooling, the reaction mixture is treated with 10.1 g (0.1 moles) of triethylamine and filtered. 195 g (96% yield) of a white solid product are obtained from the filtrate, after evaporation and subsequent drying (30° C., 10$^{-3}$ mmHg, 8 hours).

Elemental analysis (%): Experimental: Mg 9.45; Cl 57.0 Theoretical: Mg 9.71; Cl 56.68 IR analysis v (cm$^{-1}$) (nujol) 1593, 1410

\*\*Synthesis of the Titanium Compounds having General Formula (I)

The preparation of some of the compounds having general formula (I), is described hereunder. Other preparations are described in the patent application filed by the same applicant IT MI01A000858.

Example 3

Synthesis of Ti(OCOCCl$_3$)$_3$ 10.66 g of CCl$_3$COOH (65.25 mmoles) dissolved in 50 ml of n-heptane are charged into a 250 ml flask under argon. 3.13 g of TiCl$_3$ (20.30 mmoles) are added. The mixture is left under stirring at reflux temperature for 8 hours. The solid is filtered, washed with hexane and dried at room temperature for 30 hours. 9.66 g (89% yield) of brown product are obtained.

Ti: 8.70% (8.94% theoretical value) Cl (total): 57.9% (59.67% theoretical value) Cl(ionic): <1% (0% theoretical value) IR (nujol): 1609 cm$^{-1}$ ($v_{asym}$ CO$_2$); 1404 cm-1 ($v_{sym}$ CO$_2$)

Example 4

Synthesis of titanium tris-(4,4,4-trichloro-but-2-enoate) (CCl$_3$CH=CHCOO)$_3$Ti 1) Synthesis of 4,4,4-trichloro-but-2-enoic acid

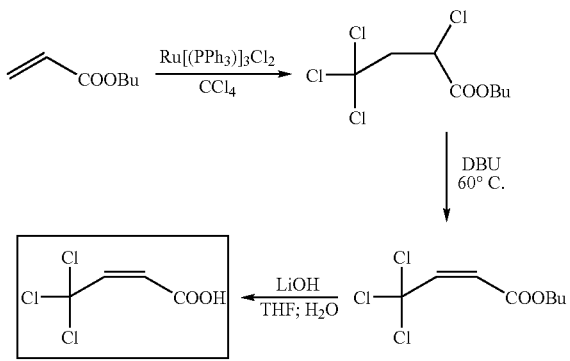

a) Synthesis of tris(triphenylphosphine)ruthenium dichloride

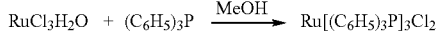

$RuCl_3H_2O + (C_6H_5)_3P \xrightarrow{MeOH} Ru[(C_6H_5)_3P]_3Cl_2$ 0.5 g of $RuCl_3 \cdot H_2O$ are dissolved, under argon, in 150 ml of anhydrous methanol and the solution is refluxed for 5 minutes. It is brought to room temperature and 2.3 g of triphenylphosphine are added. The solution is brought again to reflux temperature for three hours. It is then cooled to room temperature, filtered and the solid obtained is dried at 25° C. and $10^{-3}$ mmHg.

b) Synthesis of butyl 4,4,4,2-tetrachlorobutanoate

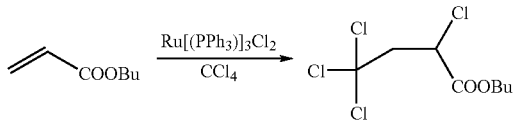

12 g of butylacrylate (94 mmoles), 200 mg of $RuCl_2[PPh_3]_3$ and 28 ml of carbon tetrachloride are charged into a 500 ml flask under argon. The mixture is brought to 90° C. for about 4 hours. Upon GC control, it is observed that the reaction is complete. The mixture is cooled, petroleum ether is added and the triphenylphosphine which precipitates is filtered. 13 g of raw residue are obtained upon evaporation of the solvent, which is used directly in the subsequent passage.

c) Synthesis of butyl 4,4,4-trichloro-but-2-enoate

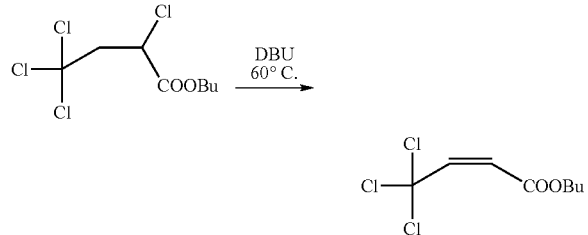

6 g of butyl 4,4,4,2-tetrachloro-butanoate (22.4 mmoles) in 20 ml of anhydrous toluene are charged under inert gas into a 250 ml flask and 5 ml of 1,8-diazabicyclo[5.4.0]undecan-7-ene (DBU) are added with exothermy. The mixture is brought to 60° C. for 3 hours. Upon GC control, it is observed that the reaction is complete; the mixture is cooled, water is added, the mixture is extracted with ethyl ether and anhydrified on $Na_2SO_4$. The residue obtained after evaporation of the solvent and purification by silica gel chromatography (eluant: hexane/ethyl acetate=9/1) weighs 4 g (76% yield).

d) Synthesis of 4,4,4-trichloro-but-2-enoic acid

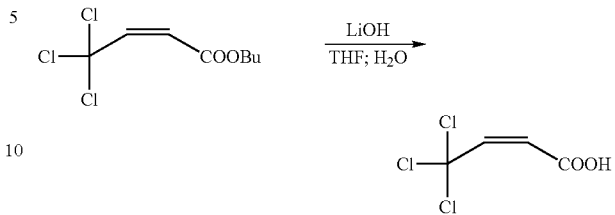

17.82 g of LiOH in 20 ml of water are added to a solution containing 3 g of butyl 4,4,4-trichloro-but-2-enoate (0.0128 moles) in 300 ml of THF. The mixture is stirred for 1 hour at room temperature. It is then brought to neutral pH with the addition of HCl 1N, extracted with ethyl acetate and anhydrified on $Na_2SO_4$. The solid obtained after evaporation of the solvent at reduced pressure and washing with petroleum ether weighs 2.1 g (87% yield).

e) Synthesis of thallium 4,4,4-trichloro-but-2-enoate $(CCl_3CH=CHCOO)Tl$ 1.56 g of 4,4,4-trichloro-but-2-enoic acid (8.4 mmoles) are added to a suspension of 1.94 g of $Tl_2CO_3$ (4.2 mmoles) in 80 ml of methanol, maintained under stirring. The mixture is left under stirring for 4 hours at room temperature. The solution is then filtered and evaporated at 15° C. and 20 mmHg. The solid obtained is washed with ethyl ether (10×50 ml) and dried at $10^{-3}$ mmHg. 3.0 g (91.2% yield) of thallium salt are obtained in the form of a white solid.

f) Synthesis of titanium tris-(4,4,4-trichloro-but-2-enoate) $(CCl_3CH=CHCOO)_3Ti$ 0.79 g (2.15 mmoles) of $TiCl_3 \cdot (THF)_3$ dissolved in 60 ml of anhydrous THF are charged under argon into a 150 ml test-tube. 3 g of $CCl_3CH=CHCOOTl$ (6.54 mmoles) are slowly added. The solution changes colour. It is left under stirring for about 4 hours. It is then filtered, evaporated and the resulting solid is dried at $10^{-3}$ mmHg for 24 hours. 1.40 g (95% yield) of complex are obtained.

Ti: 7.8%; Cl: 52.1%

Example 5

Synthesis of titanium tris-(2,4-dichloro-phenylacetate) $(2,4-Cl_2C_6H_3—CH_2—COO)_3Ti$

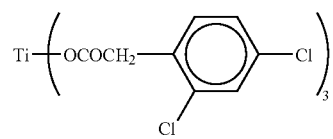

A solution of 2,4-dichlorophenylacetic acid (Acros) in toluene (11.3 g, 55 mmoles in 150 ml of solvent) is added by siphoning to a suspension of 2.8 g (18.2 mmoles) of $TiCl_3$ in 100 ml of toluene, and subsequently 0.3 ml of di-isopropylethylamine are added. The mixture is heated to reflux temperature for 5 hours. It is then cooled, the volume is reduced by evaporation under vacuum, and it is then filtered. Upon evaporation of the filtrate, 12 g (100% yield) of a bright solid product are obtained.

Ti: 7.25%; Cl: 33%

Example 6

The silica used in the present example and in the following examples was pretreated under vacuum at 160° C. for 8 hours.

Preparation of the Heterogeneous Catalyst Having the Formula $Si_{30}Mg_{4.5}Al_{0.7}Ti_1Cl_{39}$ (A)

27.5 ml of toluene (equal to the total cumulative volume of the $SiO_2$ pores plus 40%), 5.77 g (0.017 moles) of $Mg(Cl_3CCOO)_2$ and 2.21 g (0.0042 moles) of $Ti(Cl_3CCOO)_3$ (molar ratio Mg/Ti=4) are charged into a 50 ml tailed test-tube, after effecting vacuum-nitrogen and in a nitrogen atmosphere, and the mixture is left under stirring until complete dissolution.

10 g of $SiO_2$ (surface area=285 m²/g, average particle diameter=35 μm, total cumulative pore volume=1.95 ml/g, total hydroxyls=0.5 meq/g, free humidity=0.3%, total pore volume available=19.5 ml) are charged, after effecting vacuum-nitrogen and in a nitrogen atmosphere, into a 250 ml flask equipped with a propeller stirrer, drip funnel, thermometer and vacuum-nitrogen tap; at this point, the solution previously prepared is added dropwise by means of the drip funnel, maintaining the system under stirring. After the solution has been added, the mixture is kept under stirring at 30° C. for 1 h; the solvent is removed under vacuum and a solution containing 11.5 g (0.047 moles) of Ethylaluminum sesquichloride (EASC) in 27.5 ml of toluene is added dropwise (molar ratio $Cl_{EASC}$/RCOO=3). At the end of the addition, the mixture is brought to 90° C. and is kept under stirring for 2 h. It is left to cool to about 30° C., about 30 ml of toluene are added and the mixture is filtered. The solid obtained is washed three times with toluene and dried under vacuum.

The end-catalyst has the following composition: Si=16.86% by weight, Mg=2.3% by weight, Al=0.4% by weight, Ti=1.1% by weight, Cl=27.2% by weight, C=1.0% by weight ($Si_{30}Mg_{4.5}Al_{0.7}Ti_1Cl_{39}$).

Example 7

Preparation of the Heterogeneous Catalytic Component having the Formula $Si_{27.8}Mg_1Al_{0.4}Ti_1Cl_{15}$ (B)

27.5 ml of toluene (equal to the total cumulative volume of the $SiO_2$ pores plus 40%), 2.1 g (0.006 moles) of $Mg(Cl_3CCOO)_2$ and 3.1 g (0.006 moles) of $Ti(Cl_3CCOO)_3$ (molar ratio Mg/Ti=1) are charged into a 50 ml tailed test-tube, after effecting vacuum-nitrogen and in a nitrogen atmosphere, and the mixture is left under stirring until complete dissolution.

10 g of $SiO_2$ (surface area=285 m²/g, average particle diameter=35 μm, total cumulative pore volume=1.95 ml/g, total hydroxyls=0.5 meq/g, free humidity=0.3%, total pore volume available=19.5 ml) are charged, after effecting vacuum-nitrogen and in a nitrogen atmosphere, into a 250 ml flask equipped with a propeller stirrer, drip funnel, thermometer and vacuum-nitrogen tap; at this point, the solution previously prepared is added dropwise by means of the drip funnel, maintaining the system under stirring. After the solution has been added, the mixture is kept under stirring at 30° C. for 1 h; the solvent is removed under vacuum and a solution containing 7.4 g (0.03 moles) of Ethylaluminum sesquichloride (EASC) in 27.5 ml of toluene is added dropwise (molar ratio $Cl_{EASC}$/RCOO=3). At the end of the addition, the mixture is brought to 60° C. and is kept under stirring for 1 h. It is left to cool to about 30° C., about 30 ml of toluene are added and the mixture is filtered. The solid obtained is washed three times with toluene and anhydrified under vacuum.

The end-catalyst has the following composition: Si=31.1% by weight, Mg=1.0% by weight, Al=0.4% by weight, Ti=1.9% by weight, Cl=20.9% by weight, C=1.9% by weight ($Si_{27.8}Mg_1Al_{0.4}Ti_1Cl_{15}$).

Example 8

Preparation of the Catalyst Having the Formula $Si_{28.1}Mg_{0.5}Al_{0.2}Ti_1Cl_{11.9}$ (C)

27.5 ml of toluene (equal to the total cumulative volume of the $SiO_2$ pores plus 40%), 1.1 g (0.003 moles) of $Mg(Cl_3CCOO)_2$ and 3.2 g (0.006 moles) of $Ti(Cl_3CCOO)_3$ (molar ratio Mg/Ti=0.5) are charged into a 50 ml tailed test-tube, after effecting vacuum-nitrogen and in a nitrogen atmosphere, and the mixture is left under stirring until complete dissolution.

10 g of $SiO_2$ (surface area=285 m²/g, average particle diameter=35 μm, total cumulative pore volume=1.95 ml/g, total hydroxyls=0.5 meq/g, free humidity=0.3%, total pore volume available=19.5 ml) are charged, after effecting vacuum-nitrogen and in a nitrogen atmosphere, into a 250 ml flask equipped with a propeller stirrer, drip funnel, thermometer and vacuum-nitrogen tap; at this point, the solution previously prepared is added dropwise by means of the drip funnel, maintaining the system under stirring. After the solution has been added, the mixture is kept under stirring at 30° C. for 1 h; the solvent is removed under vacuum and a solution containing 1.98 g (0.024 moles) of Ethylaluminum sesquichloride (EASC) in 27.5 ml of toluene, equal to about the total pore volume available, is added dropwise (molar ratio $Cl_{EASC}$/RCOO=1). At the end of the addition, the mixture is brought to 60° C. and is kept under stirring for 1 h. It is left to cool to about 30° C., about 30 ml of toluene are added and the mixture is filtered. The solid obtained is washed three times with toluene and anhydrified under vacuum.

The end-catalyst has the following composition: Si=32.9% by weight, Mg=0.5% by weight, Al=0.18% by weight, Ti=2.0% by weight, Cl=11.9% by weight, C=2.4% by weight ($Si_{28.1}Mg_{0.5}Al_{0.2}Ti_1Cl_{11.9}$).

Example 9

Preparation of the Catalyst Having the Formula $Si_{40.3}Mg_{3.7}Al_{0.5}Ti_1Cl_{18.3}$ (D)

25 ml of toluene (equal to the total cumulative volume of the $SiO_2$ pores plus 40%), 3.74 g (0.017 moles) of $Mg(Cl_3CCOO)Cl$ and 2.23 g (0.0042 moles) of $Ti(Cl_3CCOO)_3$ (molar ratio Mg/Ti=4) are charged into a 50 ml tailed test-tube, after effecting vacuum-nitrogen and in a nitrogen atmosphere, and the mixture is left under stirring until complete dissolution.

10 g of $SiO_2$ (surface area=245 m²/g, average particle diameter=55 μm, total cumulative pore volume=1.65 ml/g, total hydroxyls=0.8 meq/g, free humidity=0.7%, total pore volume available=16.5 ml) are charged, after effecting vacuum-nitrogen and in a nitrogen atmosphere, into a 250 ml flask equipped with a propeller stirrer, drip funnel, thermometer and vacuum-nitrogen tap; at this point, the solution previously prepared is added dropwise by means of the drip funnel, maintaining the system under stirring. After the solution has been added, the mixture is kept under stirring at 30° C. for 1 h; the solvent is removed under vacuum and a solution containing 7.33 g (0.03 moles) of Ethylaluminum sesquichloride (EASC) in 25 ml of toluene is added dropwise (molar ratio $Cl_{EASC}/RCOO=3$). At the end of the addition, the mixture is brought to 90° C. and is kept under stirring for 2 h. It is left to cool to about 30° C., about 20 ml of toluene are added and the mixture is filtered. The solid obtained is washed three times with toluene and anhydrified under vacuum.

The end-catalyst has the following composition: Si=29.4% by weight, Mg=2.6% by weight, Al=0.44% by weight, Ti=1.3% by weight, Cl=19.4% by weight, C=0.8% by weight ($Si_{40.3}Mg_{3.7}Al_{0.5}Ti_1Cl_{18.3}$).

Example 10

Preparation of the Catalyst Having the Formula $Si_{27.6}Mg_{0.9}Al_{0.7}Ti_1Cl_{12.6}$ (E)

25 ml of toluene (equal to the total cumulative volume of the $SiO_2$ pores plus 40%), 1.32 g (0.006 moles) of $Mg(Cl_3CCOO)Cl$ and 3.2 g (0.006 moles) of $Ti(Cl_3CCOO)_3$ (molar ratio Mg/Ti=1) are charged into a 50 ml tailed test-tube, after effecting vacuum-nitrogen and in a nitrogen atmosphere, and the mixture is left under stirring until complete dissolution.

10 g of $SiO_2$ (surface area=245 m²/g, average particle diameter=55 µm, total cumulative pore volume=1.65 ml/g, total hydroxyls=0.8 meq/g, free humidity=0.7%, total pore volume available 16.5 ml) are charged, after effecting vacuum-nitrogen and in a nitrogen atmosphere, into a 250 ml flask equipped with a propeller stirrer, drip funnel, thermometer and vacuum-nitrogen tap; at this point, the solution previously prepared is added dropwise by means of the drip funnel, maintaining the system under stirring. After the solution has been added, the mixture is kept under stirring at 30° C. for 1 h; the solvent is removed under vacuum and a solution containing 5.94 g (0.024 moles) of Ethylaluminum sesquichloride (EASC) in 25 ml of toluene is added dropwise (molar ratio $Cl_{EASC}/RCOO=3$). At the end of the addition, the mixture is brought to 60° C. and is kept under stirring for 1 h. It is left to cool to about 30° C., about 20 ml of toluene are added and the mixture is filtered. The solid obtained is washed three times with toluene and anhydrified under vacuum.

The end-catalyst has the following composition: Si=32.4% by weight, Mg=1.0% by weight, Al=0.80% by weight, Ti=2.0% by weight, Cl=18.8% by weight, C=1.6% by weight ($Si_{27.6}Mg0.9Al_{0.7}Ti_1Cl_{12.6}$).

Example 11

Preparation of the Catalyst Having the Formula $Si_{59.4}Mg_{4.1}Al_{0.8}Ti_1Cl_{34.7}$ (F)

27.5 ml of toluene (equal to the total cumulative volume of the $SiO_2$ pores plus 40%), 4.82 g (0.012 moles) of $Mg(Cl_3C(CH_2)_2COO)_2$ and 1.85 g (0.003 moles) of $Ti(Cl_3C(CH_2)_2COO)_3$ (molar ratio Mg/Ti=4) are charged into a 50 ml tailed test-tube, after effecting vacuum-nitrogen and in a nitrogen atmosphere, and the mixture is left under stirring until complete dissolution.

10 g of $SiO_2$ (surface area=285 m²/g, average particle diameter=35 µm, total cumulative pore volume=1.95 ml/g, total hydroxyls=0.5 meq/g, free humidity=0.3%, total pore volume available=19.5 ml) are charged, after effecting vacuum-nitrogen and in a nitrogen atmosphere, into a 250 ml flask equipped with a propeller stirrer, drip funnel, thermometer and vacuum-nitrogen tap; at this point, the solution previously prepared is added dropwise by means of the drip funnel, maintaining the system under stirring. After the solution has been added, the mixture is kept under stirring at 30° C. for 1 h; the solvent is removed under vacuum and a solution containing 8.2 g (0.033 moles) of Ethylaluminum sesquichloride (EASC) in 27.5 ml of toluene is added dropwise (molar ratio $Cl_{EASC}/RCOO=3$). At the end of the addition, the mixture is brought to 90° C. and is kept under stirring for 2 h. It is left to cool to about 30° C., about 30 ml of toluene are added and the mixture is filtered. The solid obtained is washed three times with toluene and dried under vacuum.

The end-catalyst has the following composition: Si=28.2% by weight, Mg=1.7% by weight, Al=0.37% by weight, Ti=0.8% by weight, Cl=20.8% by weight, C=2.1% by weight ($Si_{59.4}Mg_{4.1}Al_{0.8}Ti_1Cl_{34.7}$).

Example 12

Preparation of the Heterogeneous Catalytic Component Having the Formula $Si_{45.5}Mg_{4.5}Al_{0.8}Ti_1Cl_{38}$ (G)

27.5 ml of toluene (equal to the total cumulative volume of the $SiO_2$ pores plus 40%), 5.77 g (0.017 moles) of $Mg(Cl_3CCOO)_2$ and 2.58 g (0.0042 moles) of $Ti(Cl_3C(CH_2)_2COO)_3$ (molar ratio Mg/Ti=4) are charged into a 50 ml tailed test-tube, after effecting vacuum-nitrogen and in a nitrogen atmosphere, and the mixture is left under stirring until complete dissolution.

10 g of $SiO_2$ (surface area=285 m²/g, average particle diameter=35 µm, total cumulative pore volume=1.95 ml/g, total hydroxyls=0.5 meq/g, free humidity=0.3%, total pore volume available=19.5 ml) are charged, after effecting vacuum-nitrogen and in a nitrogen atmosphere, into a 250 ml flask equipped with a propeller stirrer, drip funnel, thermometer and vacuum-nitrogen tap; at this point, the solution previously prepared is added dropwise by means of the drip funnel, maintaining the system under stirring. After the solution has been added, the mixture is kept under stirring at 30° C. for 1 h; the solvent is removed under vacuum and a solution containing 11.5 g (0.047 moles) of Ethylaluminum sesquichloride (EASC) in 27.5 ml of toluene is added dropwise (molar ratio $Cl_{EASC}/RCOO=3$). At the end of the addition, the mixture is brought to 90° C and is kept under stirring for 2 h. It is left to cool to about 30° C., about 30 ml of toluene are added and the mixture is filtered. The solid obtained is washed three times with toluene and dried under vacuum.

The end-catalyst has the following composition: Si=25.6% by weight, Mg=2.2% by weight, Al=0.43% by weight, Ti=1.1% by weight, Cl=26.7% by weight, C=1.1% by weight ($Si_{45.5}Mg_{4.5}Al_{0.8}Ti_1Cl_{38}$).

Example 13

Preparation of the Catalyst Having the Formula $Si_{41.2}Mg_4Al_{0.7}Ti_1Cl_{34}$ (H)

27.5 ml of toluene (equal to the total cumulative volume of the $SiO_2$ pores plus 40%), 5.88 g (0.017 moles) of $Mg(Cl_3CCOO)_2$ and 2.59 g (0.0042 moles) of $Ti(Cl_3CCH=CHCOO)_3$ (molar ratio Mg/Ti=4) are charged into a 50 ml tailed test-tube, after effecting vacuum-nitrogen and in a nitrogen atmosphere, and the mixture is left under stirring until complete dissolution.

10 g of $SiO_2$ (surface area=285 m²/g, average particle diameter=35 µm, total cumulative pore volume=1.95 ml/g, total hydroxyls=0.5 meq/g, free humidity=0.3%, total pore volume available=19.5 ml) are charged, after effecting vacuum-nitrogen and in a nitrogen atmosphere, into a 250 ml flask equipped with a propeller stirrer, drip funnel, thermometer and vacuum-nitrogen tap; at this point, the solution previously prepared is added dropwise by means of the drip funnel, maintaining the system under stirring. After the solution has been added, the mixture is kept under stirring at 30° C. for 1 h; the solvent is removed under vacuum and a solution containing 11.5 g (0.047 moles) of Ethylaluminum sesquichloride (EASC) in 27.5 ml of toluene is added dropwise (molar ratio $Cl_{EASC}$/RCOO=3). At the end of the addition, the mixture is brought to 90° C. and is kept under stirring for 2 h. It is left to cool to about 30° C., about 30 ml of toluene are added and the mixture is filtered. The solid obtained is washed three times with toluene and dried under vacuum.

The end-catalyst has the following composition: Si=28.8% by weight, Mg=2.5% by weight, Al=0.47% by weight, Ti=1.2% by weight, Cl=29.9% by weight, C=0.9% by weight ($Si_{41.2}Mg_4Al_{0.7}Ti_1Cl_{34}$).

Example 14

Preparation of the Catalyst Having the Formula $Si_{40}Mg_{3.9}Al_{0.9}Ti_1Cl_{29.6}$ (L)

27.5 ml of toluene (equal to the total cumulative volume of the $SiO_2$ pores plus 40%), 5.89 g (0.017 moles) of $Mg(Cl_2CCOO)_2$ and 2.76 g (0.0042 moles) of $Ti(2,4-Cl_2C_6H_3CH_2COO)_3$ (molar ratio Mg/Ti=4) are charged into a 50 ml tailed test-tube, after effecting vacuum-nitrogen and in a nitrogen atmosphere, and the mixture is left under stirring until complete dissolution.

10 g of $SiO_2$ (surface area=285 m$^2$/g, average particle diameter=35 μm, total cumulative pore volume=1.95 ml/g, total hydroxyls=0.5 meq/g, free humidity=0.3%, total pore volume available=19.5 ml) are charged, after effecting vacuum-nitrogen and in a nitrogen atmosphere, into a 250 ml flask equipped with a propeller stirrer, drip funnel, thermometer and vacuum-nitrogen tap; at this point, the solution previously prepared is added dropwise by means of the drip funnel, maintaining the system under stirring. After the solution has been added, the mixture is kept under stirring at 30° C. for 1 h; the solvent is removed under vacuum and a solution containing 11.5 g (0.047 moles) of Ethylaluminum sesquichloride (EASC) in 27.5 ml of toluene is added dropwise (molar ratio $Cl_{EASC}$/RCOO=3). At the end of the addition, the mixture is brought to 90° C. and is kept under stirring for 2 h. It is left to cool to about 30° C., about 30 ml of toluene are added and the mixture is filtered. The solid obtained is washed three times with toluene and dried under vacuum.

The end-catalyst has the following composition: Si=25.8% by weight, Mg=2.2% by weight, Al=0.52% by weight, Ti=1.1% by weight, Cl=23.9% by weight, C=1.7% by weight ($Si_{40}Mg_{3.9}Al_{0.9}Ti_1Cl_{29.6}$).

Examples 15-20

Polymerization of propylene in Solution

Vacuum-nitrogen is effected for at least three times at 90° C. and for an overall duration of about 2 hours, in a Buchi autoclave with a 1 liter steel reactor, equipped with a burette for the feeding of the catalyst, propeller stirrer, thermo-resistance and heating jacket connected to a thermostat for the temperature control. A flushing of the reactor is carried out before each test, maintaining a solution containing 250 ml of anhydrous heptane and 2.5 ml of Al(i-Bu)$_3$ under stirring at 90° C. for about 2 hours. The contents of the reactor are discharged through a valve situated on the bottom under a slight nitrogen pressure and a solution containing 500 ml of heptane and 0.2 ml of Al(i-Bu)$_3$ (0.8 mmoles) are charged into the autoclave. The autoclave is pressurized by introducing 33 g of propylene (4 ata) (measured by means of a HI-TECH flow-rate meter model F 201 C-FA-22-V-M FC) and the whole apparatus is thermostat-regulated at 65° C. At this point, a suspension of the Ti catalyst (Ti=0.002 mmoles, molar ratio Al/Ti=400) in 10 ml of heptane is charged by means of a slight nitrogen overpressure, through the burette situated at the head of the autoclave. Once the catalyst has been charged, the system is brought to 7 ata by feeding propylene. The system is maintained for 1 hour at this pressure (7 ata) by means of a stream of propylene. At the end, the contents of the reactor are discharged under pressure by means of the valve situated on the bottom and coagulated in about 1 liter of ethanol. The polymer obtained (polypropylene) is separated by means of filtration, washed with acetone and dried under vacuum at 40° C. for about 8 hours.

Table 2 indicates the results obtained.

Examples 21-24

Copolymerization of propylene-ethylene in Solution

Vacuum-nitrogen is effected for at least three times at 90° C. and for an overall duration of about 2 hours, in a Buchi autoclave with a 1 liter steel reactor, equipped with a burette for the feeding of the catalyst, propeller stirrer, thermo-resistance and heating jacket connected to a thermostat for the temperature control. A flushing of the reactor is carried out before each test, maintaining a solution containing 250 ml of anhydrous heptane and 2.5 ml of Al(i-Bu)$_3$ under stirring at 90° C. for about 2 hours. The contents of the reactor are discharged through a valve situated on the bottom under a slight nitrogen pressure and a solution containing 500 ml of heptane and 0.2 ml of Al(i-Bu)$_3$ (0.8 mmoles) are charged into the autoclave. The autoclave is pressurized by introducing in order: propylene (33 g, 4 ata) and ethylene in the quantity specified in Table 3 (measured by means of a HI-TECH flow-rate meter model F 201 C-FA-22-V-M FC) and the whole apparatus is thermostat-regulated at 65° C. At this point, a suspension of the Ti catalyst (Ti=0.01 mmoles, molar ratio Al/Ti=800) in 10 ml of heptane is charged by means of a slight nitrogen overpressure, through the burette situated at the head of the autoclave. Once the catalyst has been charged, the system is brought to 7 ata with propylene and is maintained for 1 hour at a constant pressure by means of a stream of propylene (7 ata). At the end, the contents of the reactor are discharged under pressure by means of the valve situated on the bottom and coagulated in about 1 liter of ethanol. The polymer obtained is separated by means of filtration, washed with acetone and dried under vacuum at 40° C. for about 8 hours.

Table 3 indicates the results obtained.

Examples 25-28

Polymerization of hexene in Solution

Vacuum-nitrogen is effected for at least three times in a 250 ml glass flask equipped with a propeller stirrer.

The following products are introduced in order: 100 ml of heptane, 12 ml (8 g) of 1-hexene, 0.25 ml (1.0 mmoles) of Al(i-Bu)$_3$; a suspension of the Ti catalyst (Ti=0.1 mmoles, molar ratio Al/Ti=10) in 10 ml of heptane is then added. Once the catalyst has been charged, the mixture is left for 5 hours at about 40° C. At the end, the contents of the flask are discharged and coagulated in about 600 ml of methanol. The polymer is separated by means of filtration, washed with acetone and dried under vacuum at 40° C. for about 8 hours.

The results obtained are indicated in Table 4.

Examples 29-31

Terpolymerization of ethylene-propylene-5-ethylidene-2-norbornene (ENB) in Solution Vacuum-nitrogen is effected for at least three times at 90° C. and for an overall duration of about 2 hours, in a Buchi autoclave with a 2 liter steel reactor, equipped with a burette for the feeding of the catalyst, propeller stirrer, thermo-resistance and heating jacket connected to a thermostat for the temperature control. A flushing of the reactor is carried out before each test, maintaining a solution containing 500 ml of anhydrous heptane and 5 ml of Al(i-Bu)$_3$ under stirring at 90° C. for about 2 hours. The contents of the reactor are discharged through a valve situated on the bottom under a slight nitrogen pressure and a solution containing 1 liter of heptane, 10 ml of ENB (75 mmoles) and 0.53 ml of Al(i-Bu)$_3$ (2.1 mmoles) are charged into the autoclave. The autoclave is pressurized by introducing in order: 200 g of propylene (4.9 ata) and 7 g of ethylene (1 ata) (measured by means of a HI-TECH flow-rate meter model F 201 C-FA-22-V-M FC) and the whole apparatus is thermostat-regulated at 30° C. At this point, a suspension of the Ti catalyst (Ti=0.042 mmoles, molar ratio Al/Ti=50) in 10 ml of heptane is charged by means of a slight nitrogen overpressure, through the burette situated at the head of the autoclave. Once the catalyst has been charged, the system is brought to 7 ata by means of ethylene and is maintained at this pressure for 1 hour by means of a stream of ethylene. At the end, the contents of the reactor are discharged under pressure by means of the valve situated on the bottom and coagulated in about 3 liters of ethanol. The polymer obtained is separated by means of filtration, washed with acetone and dried under vacuum at 40° C. for about 8 hours.

The results of the relative experimentation are indicated in Table 5.

Examples 32-34

Copolymerization of ethylene-propylene in Liquid propylene

Vacuum-nitrogen is effected for at least three times at 90° C. and for an overall duration of about 2 hours, in a Buchi autoclave with a 500 ml steel reactor, equipped with a burette for the feeding of the catalyst, propeller stirrer, thermo-resistance and heating jacket connected to a thermostat for the temperature control. A flushing of the reactor is carried out before each test, maintaining a solution containing 100 ml of anhydrous heptane and 1 ml of Al(i-Bu)$_3$ under stirring at 90° C. for about 2 hours. The contents of the reactor are discharged through a valve situated on the bottom under a slight nitrogen pressure and 120 g of liquid propylene are charged into the autoclave at 23° C. The reactor is then brought to the polymerization temperature of 40° C. and 0.53 ml of Al(i-Bu)$_3$ (2.1 mmoles) are introduced; gaseous ethylene is subsequently charged until the equilibrium pressure is reached (20-22 ata). At this point, a suspension of the Ti catalyst (Ti=0.042 mmoles, molar ratio Al/Ti=50) in 10 ml of heptane is charged by means of a slight nitrogen overpressure, through the burette situated at the head of the autoclave. Once the catalyst has been charged, the system is left for 1 hour and is maintained at a constant pressure by means of a stream of ethylene. At the end, the polymerization is stopped by the rapid degassing of the residual monomers. The polymer is recovered, after washing with ethyl alcohol and dried at 40° C. for about 8 h under vacuum.

The results of the relative experimentation are indicated in Table 6.

Example 35

Polymerization of ethylene-propylene in Slurry

Vacuum-nitrogen is effected for at least three times at 90° C. and for an overall duration of about 2 hours, in a Buchi autoclave with a 1 liter steel reactor, equipped with a burette for the feeding of the catalyst, propeller stirrer, thermo-resistance and heating jacket connected to a thermostat for the temperature control. A flushing of the reactor is carried out before each test, maintaining a solution containing 500 ml of anhydrous heptane and 5 ml of Al(i-Bu)$_3$ under stirring at 90° C. for about 2 hours. The contents of the reactor are discharged through a valve situated on the bottom under a slight nitrogen pressure and a solution containing 1 liter of heptane and 0.53 ml of Al(i-Bu)$_3$ (2.1 mmoles) are charged into the autoclave. The autoclave is pressurized by introducing 100 g of propylene (3.5 ata) and 7 grams (1 ata) of ethylene (measured by means of a HI-TECH flow-rate meter model F 201 C-FA-22-V-M FC) and the whole apparatus is thermostat-regulated at 30° C. At this point, a suspension of the catalyst C (Ti=0.042 mmoles, molar ratio Al/Ti=50) in 10 ml of heptane is charged by means of a slight nitrogen overpressure, through the burette situated at the head of the autoclave. Once the catalyst has been charged, the system is brought to 7 ata with ethylene and is maintained at a constant pressure (7 ata) by means of a stream of propylene. At the end, the contents of the reactor are discharged under pressure by means of the valve situated on the bottom and coagulated in about 1 liter of ethanol. The polymer is separated by means of filtration, washed with acetone and dried under vacuum at 40° C. for about 8 hours.

16.4 g (285 kg$_{Pol}$/g$_{Ti}$) of a free-flowing ethylene-propylene copolymer are obtained, containing 12.4% in moles of propylene, $r_E \times r_P = 1.2$, Mw=390000, MWD=3.6 and having an average particle diameter of 220 μm.

Examples 36-37

Copolymerization of ethylene-norbornene (NB) in Solution

Vacuum-nitrogen is effected for at least three times at 90° C. and for an overall duration of about 2 hours, in a Buchi autoclave with a 2 liter steel reactor, equipped with a burette for the feeding of the catalyst, propeller stirrer, thermo-resistance and heating jacket connected to a thermostat for the temperature control. A flushing of the reactor is carried out before each test, maintaining a solution containing 500 ml of anhydrous heptane and 5 ml of Al(i-Bu)$_3$ under stirring at 90° C. for about 2 hours. The contents of the reactor are discharged through a valve situated on the bottom under a slight nitrogen pressure and a solution containing 1 liter of heptane, NB (in the quantity indicated in Table 7) and 0.53 ml of Al(i-Bu)$_3$ (2.1 mmoles) are charged into the autoclave. The whole system is thermostat-regulated at 30° C. and a suspension of the Ti catalyst (Ti=0.042 mmoles, molar ratio Al/Ti=50) in 10 ml of heptane is charged by means of a slight nitrogen overpressure, through the burette situated at the head of the autoclave. Once the catalyst has been charged, the system is left to run for 1 hour and is maintained at a constant pressure (3 ata) by means of a stream of ethylene. At the end, the contents of the reactor are discharged under pressure by means of the valve situated on the bottom and coagulated in about 3 liters of ethanol. The polymer is separated by means of filtration, washed with acetone and dried under vacuum at 40° C. for about 8 hours.

The results of the relative experimentation are indicated in Table 7.

TABLE 1

SUMMARY OF HETEROGENEOUS CATALYSTS

| Example | Abbrev. | Magnesium complex | Titanium complex | Mg/Ti | $Cl_{EASC}/RCOO$ | Atomic composition |
|---|---|---|---|---|---|---|
| 6 | A | $Mg(Cl_3CCOO)_2$ | $Ti(Cl_3CCOO)_3$ | 4 | 3 | $Si_{30}Mg_{4.5}Al_{0.7}Ti_1Cl_{30}$ |
| 7 | B | $Mg(Cl_3CCOO)_2$ | $Ti(Cl_3CCOO)_3$ | 1 | 3 | $Si_{27.8}Mg_1Al_{0.4}Ti_1Cl_{15}$ |
| 8 | C | $Mg(Cl_3CCOO)_2$ | $Ti(Cl_3CCOO)_3$ | 0.5 | 1 | $Si_{28.1}Mg_{0.5}Al_{0.2}Ti_1Cl_{11.9}$ |
| 9 | D | $Mg(Cl_3CCOO)Cl$ | $Ti(Cl_3CCOO)_3$ | 4 | 3 | $Si_{40.3}Mg_{3.7}Al_{0.5}Ti_1Cl_{18.3}$ |
| 10 | E | $Mg(Cl_3CCOO)Cl$ | $Ti(Cl_3CCOO)_3$ | 1 | 3 | $Si_{27.6}Mg_{0.8}Al_{0.7}Ti_1Cl_{12.6}$ |
| 11 | F | $Mg(Cl_3C(CH_2)_2COO)_2$ | $Ti(Cl_3C(CH_2)_2COO)_3$ | 4 | 3 | $Si_{59.4}Mg_{4.1}Al_{0.8}Ti_1Cl_{34.7}$ |
| 12 | G | $Mg(Cl_3CCOO)_2$ | $Ti(Cl_3C(CH_2)_2COO)_3$ | 4 | 3 | $Si_{45.5}Mg_{4.5}Al_{0.8}Ti_1Cl_{38}$ |
| 13 | H | $Mg(Cl_3CCOO)_2$ | $Ti(Cl_3CCH=CHCOO)_3$ | 4 | 3 | $Si_{41.2}Mg_4Al_{0.7}Ti_1Cl_{34}$ |
| 14 | L | $Mg(Cl_3CCOO)_2$ | $Ti(2,4-Cl_2C_6H_3CH_2COO)_3$ | 4 | 3 | $Si_{40}Mg_{3.9}Al_{0.9}Ti_1Cl_{29.6}$ |

TABLE 2

SUPPORTED CATALYSTS BASED ON TITANIUM POLYMERIZATION OF PROPYLENE

| Example | Catalyst | Activity $Kg_{Pol}/g_n$ | m/r | $M_w \times 10^{-3}$ | MWD |
|---|---|---|---|---|---|
| 15 | $Si_{30}Mg_{4.5}Al_{0.7}Ti_1Cl_{39}$ (A) | 250 | 62/38 | 197 | 6.7 |
| 16 | $Si_{40.3}Mg_{3.7}Al_{0.5}Ti_1Cl_{18.3}$ (D) | 180 | 60/40 | 442 | 7.6 |
| 17 | $Si_{59.4}Mg_{4.1}Al_{0.8}Ti_1Cl_{34.7}$ (F) | 340 | 60/40 | 162 | 4.7 |
| 18 | $Si_{45.5}Mg_{4.5}Al_{0.8}Ti_1Cl_{38}$ (G) | 287 | 61/39 | 191 | 4.3 |
| 19 | $Si_{41.2}Mg_4Al_{0.7}Ti_1Cl_{34}$ (H) | 180 | 63/37 | 361 | 4.5 |
| 20 | $Si_{40}Mg_{3.9}Al_{0.9}Ti_1Cl_{29.6}$ (L) | 125 | 65/35 | 357 | 7.6 |

TABLE 3

SUPPORTED CATALYSTS BASED ON TITANIUM
PROPYLENE-ETHYLENE COPOLYMERIZATION IN SOLUTION

| Example | Catalyst | $C_2$ feeding g (ata) | Activity $Kg_{Pol}/g_n$ | $C_2$ bound % moles | $M_w \times 10^{-3}$ | MWD |
|---|---|---|---|---|---|---|
| 21 | $Si_{27.8}Mg_1Al_{0.4}Ti_1Cl_{15}$ (B) | 0.5 (0.5) | 280 | 8.3 | 308 | 6.6 |
| 22 | $Si_{30}Mg_{4.5}Al_{0.7}Ti_1Cl_{39}$ (A) | 0.5 (0.5) | 335 | 4.1 | 192 | 6.7 |
| 23 | $Si_{59.4}Mg_{4.1}Al_{0.8}Ti_1Cl_{34.7}$ (F) | 1.0 (0.7) | 412 | 2.7 | 224 | 4.7 |
| 24 | $Si_{45.5}Mg_{4.5}Al_{0.8}Ti_1Cl_{38}$ (G) | 1.5 (0.9) | 420 | 3.3 | 442 | 5.5 |

TABLE 4

SUPPORTED CATALYSTS BASED ON TITANIUM
POLYMERIZATION OF 1-HEXENE

| Example | Catalyst | Yield g | Activity $g_{Pol}/g_n$ | Conversion % | $M_w \times 10^{-3}$ | MWD |
|---|---|---|---|---|---|---|
| 25 | $Si_{30}Mg_{4.5}Al_{0.7}Ti_1Cl_{39}$ (A) | 7.8 | 1625 | 98 | 543 | 4.7 |
| 26 | $Si_{40.3}Mg_{3.7}Al_{0.5}Ti_1Cl_{18.3}$ (D) | 5.0 | 1040 | 62 | 399 | 4.3 |
| 27 | $Si_{59.4}Mg_{4.1}Al_{0.8}Ti_1Cl_{34.7}$ (F) | 8.0 | 1670 | 100 | 447 | 2.9 |
| 28 | $Si_{45.5}Mg_{4.5}Al_{0.8}Ti_1Cl_{38}$ (G) | 7.7 | 1600 | 97 | 343 | 3.5 |

TABLE 5

SUPPORTED CATALYSTS BASED ON TITANIUM
ETHYLENE-PROPYLENE-ENB TERPOLYMERIZATION IN SOLUTION

| Example | Catalyst | Activity $kg_{Pol}/g_n$ | $C_3$ % moles | ENB % moles | $r_E \times r_P$ | $M_w \times 10^{-3}$ | MWD |
|---|---|---|---|---|---|---|---|
| 29 | $Si_{27.8}Mg_1Al_{0.4}Ti_1Cl_{15}$ (B) | 95 | 27.3 | 1.5 | 1.41 | 459 | 4.3 |
| 30 | $Si_{28.1}Mg_{0.5}Al_{0.2}Ti_1Cl_{11.9}$ (C) | 72 | 32.7 | 1.1 | 1.12 | 230 | 4.6 |
| 31 | $Si_{27.6}Mg_{0.9}Al_{0.7}Ti_1Cl_{12.6}$ (E) | 80 | 30.8 | 1.4 | 1.45 | 261 | 4.7 |

TABLE 6

SUPPORTED CATALYSTS BASED ON TITANIUM
ETHYLENE-PROPYLENE COPOLYMERIZATION IN LIQUID MONOMER

| Example | Catalyst | Activity $kg_{Pol}/g_n$ | $C_3$ % moles | $r_E \times r_P$ | $M_w \times 10^{-3}$ | MWD |
|---|---|---|---|---|---|---|
| 32 | $Si_{27.8}Mg_1Al_{0.4}Ti_1Cl_{15}$ (B) | 300 | 27.5 | 1.16 | 456 | 6.6 |
| 33 | $Si_{28.1}Mg_{0.5}Al_{0.2}Ti_1Cl_{11.9}$ (C) | 250 | 30.8 | 0.95 | 311 | 6.2 |
| 34 | $Si_{27.6}Mg_{0.9}Al_{0.7}Ti_1Cl_{12.8}$ (E) | 270 | 28.1 | 1.21 | 215 | 6.1 |

TABLE 7

SUPPORTED CATALYSTS BASED ON TITANIUM
ETHYLENE-NORBORNENE COPOLYMERIZATION IN SOLUTION

| Example | Catalyst | NB feeding moles | Activity $kg_{Pol}/g_n$ | NB bound % moles | Tg [° C.] | $M_w \times 10^{-3}$ | MWD |
|---|---|---|---|---|---|---|---|
| 36 | $Si_{30}Mg_{4.5}Al_{0.7}Ti_1Cl_{39}$ (A) | 0.73 | 191 | 2.2 | 130 | 180 | 5.4 |
| 37 | $Si_{30}Mg_{4.5}Al_{0.7}Ti_1Cl_{39}$ (A) | 1.10 | 68 | 4.1 | 122 | 142 | 5.7 |

Comments on the Table

All the catalysts indicated in Table 1 produce polymers with high Mw values. Furthermore, the yields are much higher than the corresponding titanium complexes used as such and disclosed in the copending patent application filed by the same applicant (IT MI01A000858).

From Table 2, it can be observed that with a decrease in the quantity of chlorine in the catalyst, there is a reduction in the catalytic activity (compare examples 15 and 16). The catalytic activity increases moreover with a lengthening in the chlorocarboxylic chain of the ligand present both in the titanium complex (compare examples 15, 18) and in the magnesium complex (compare examples 17 and 18). All the polypropylenes produced are prevalently of atactic-type polymers (m/r about 60/40), whereas the molecular weight distributions vary from 4 to 8, showing a tendency towards lower values with a lengthening of the chain on the chlorocarboxylic ligand present in the titanium complex (compare examples 15 and 16 with 17-19).

The use of ethylene in the polymerization causes an increase in the catalytic activity (compare example 15 of Table 2 with 22 of Table 3). From Table 3 it can also be observed that the catalysts with an Mg/Ti ratio=1 incorporate more ethylene with respect to those with an Mg/Ti ratio=4 (compare examples 21 and 22) whereas the presence of long-chain chlorocarboxylic ligands also produces, in this case, lower MWD values (examples 23 and 24).

Table 4 relating to the polymerization of hexene shows high conversion values with respect to the monomer fed (>95%) when catalysts with a high chlorine content are used, whereas there are low conversion values with a decrease in the chlorine content (compare examples 25 and 26). The Mw values are higher than 300000 whereas the MWD values vary within the range of 3 to 5.

From the data of Table 5 relating to EPDM terpolymers and Table 6 relating to EPR copolymers, a slight decrease in the activity is observed with a decrease in the chlorine content (compare example 29 with 30-31 of Table 5 and example 32 with 33-34 of Table 6) and also a tendency to decrease the $r_E \times r_P$ values with a decrease in the Mg/Ti ratio (compare examples 29-31 with 30 of Table 5 and examples 32-34 with 33 of Table 6). The characteristics of the relative polymers do not significantly change with a variation in the atomic composition of the catalysts under examination.

Finally, Table 7 indicates ethylene-norbornene co-polymerization tests specifying the characteristics of the polymers obtained using a single catalyst with an Mg/Ti ratio=4.

The invention claimed is:

1. A catalyst supported on silica, active in the polymerization, copolymerization and terpolymerization of olefin-unsaturated compounds, wherein the silica has a surface area of $\geq 200$ m$^2$/g, a total cumulative pore volume greater than 1 ml/g, as measured by the BET method, a quantity of total surface hydroxyls (isolated, vicinal, geminal) of less than 1.0 milliequivalents (meq)/g, an average particle diameter ranging from 5 μm to 100 μm, a free humidity content lower than or equal to 2% by weight, and wherein the catalyst contains from 0.5 to 3.0% by weight of titanium with respect to the total weight of the catalyst, and further contains Si, Mg, Al and Cl in the following atomic composition with respect to titanium:

$$Ti_1Mg_{0.5-10}Al_{0.2-1}Cl_{5-40}Si_{20-70}$$

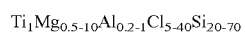

and is obtained by means of a process which comprises:
(i) deposition in the pores of the above silica of at least one solution of (i1) at least one derivative of magnesium selected from bis magnesium chlorocarboxylates and halogen magnesium chlorocarboxylates having general formula (II)

$$MgX'_m(R'-COO)_{(2-m)} \quad (II)$$

wherein
X' is a halogen, excluding iodine;
m is selected from 0 to 1;
R' is a chlorinated monofunctional hydrocarbyl radical having from 1 to 20 carbon atoms and from 1 to 6 chlorine atoms;
and of (i2) at least one derivative of titanium selected from titanium chlorocarboxylates having general formula (I):

$$(RCOO)_nTiX_p \quad (I)$$

wherein:
p+n=2, 3, 4;
n≧1;
R has the same meaning as R';
X is selected from chlorine, bromine, alkoxyl, carboxyl, beta-dicarbonyl group;
and wherein the atomic ratio between the Mg in (II) and Ti in (I) ranges from 0.5/1 to 10/1;
(ii) subsequent deposition, on the silica containing derivatives of magnesium and titanium obtained at the end of step (i), of a solution of one or more halogen alkyl derivatives of aluminum selected from those having general formula (III) and (IV):

$$AlR''_nX''_{3-n} \text{ (with n=1 or 2)} \quad (III)$$

$$Al_2R''_nX''_{6-n} \text{ (n=1 to 5)} \quad (IV)$$

wherein
R" is a $C_1$-$C_{20}$ alkyl group,
X" is chlorine or bromine;
and wherein the ratio between the sum of the halogen atoms in (III) and/or (IV) and the total carboxyl groups in (I) and (II) varies from 0.3/1 to 10/1;
(iii) reaction, inside the silica pores containing derivatives of Ti, Mg, Al obtained at the end of step (ii), between the one or more halogen alkyl derivatives of aluminum and compounds (I) and (II), thus obtaining a supported catalyst consisting of porous silica containing, inside the pores, derivatives of magnesium, titanium, aluminum and by-products essentially based on aluminum;
(iv) recovery of the supported catalyst obtained at the end of step (iii), after elimination by washing the aluminum-based by-products.

2. The catalyst supported on silica according to claim 1, wherein the silica has a surface area ranging from 250 to 400 m²/g.

3. The catalyst supported on silica according to claim 1, wherein the silica has a cumulative pore volume ranging from 1.1 to 3 ml/g.

4. The catalyst supported on silica according to claim 3, wherein the silica has a cumulative pore volume ranging from 1.2 to 2.0 ml/g.

5. The catalyst supported on silica according to claim 1, wherein the silica has a quantity of total surface hydroxyls (isolated, vicinal, geminal) ranging from 0.4 to 0.6 meq/g.

6. The catalyst supported on silica according to claim 1, wherein the silica has an average particle diameter ranging from 20 μm to 60 μm.

7. The catalyst supported on silica according to claim 1, wherein the silica has a humidity of less than 1% by weight.

8. The catalyst supported on silica according to claim 1, wherein X=X'=X"=Cl.

9. The catalyst supported on silica according to claim 1, wherein R and R', the same or different, are monofunctional hydrocarbyl radicals having from 1 to 20 carbon atoms and from 1 to 6 chlorine atoms.

10. The catalyst supported on silica according to claim 1, wherein the ratio between the sum of the halogen atoms in (III) and/or (IV) and the total carboxyl groups in (I) and (II) varies from 0.5/1 to 4.0/1.

11. The catalyst supported on silica according to claim 1, wherein p+n=3.

12. The catalyst supported on silica according to claim 1, wherein the titanium content ranges from 0.6 to 3.0% by weight.

13. The catalyst supported on silica according to claim 12, wherein the titanium content ranges from 0.6 to 2.0% by weight.

14. The catalyst supported on silica according to claim 1, wherein RCOO and R'COO, the same or different, are selected from $CCl_3COO$, $CCl_3(CH_2)_2COO$, $Cl_2C_6H_3CH_2COO$, $CCl_3CH=CHCOO$.

15. The catalyst supported on silica according to claim 1, wherein step (i) comprises:
(ia) preparation of a hydrocarbon solution of the compounds having general formula (I) and (II);
(ib) treatment of the silica with a volume of the solution of (I) and (II) from 15% to 50% higher than the total cumulative pore volume of the silica, the above treatment being prolonged until the almost complete deposition of compounds (I) and (II) in the silica pores;
(ic) elimination of the solvent used to dissolve compounds (I) and (II).

16. The catalyst supported on silica according to claim 15, wherein step (ib) consists in the treatment of the silica with a volume of the solution of (I) and (II) from 20% to 45% higher than the total cumulative volume of the silica pores.

17. The catalyst supported on silica according to claim 1, wherein step (ii) comprises:
(iia) dissolution of one or more halogen alkyl derivatives of aluminum having general formula (III) and/or (IV) in a suitable inert solvent;
(iib) treatment of the silica obtained at the end of step (i) with a volume of the solution (iia) from 15% to 50% higher than the total cumulative volume of the silica pores.

18. The catalyst supported on silica according to claim 1, wherein step (iii) is effected by heating the silica obtained at the end of step (ii), to a temperature ranging from 30° C. to 120° C.

19. The catalyst supported on silica according to claim 18, wherein step (iii) is effected by heating the silica obtained at the end of step (ii) to a temperature ranging from 40° C. to 100° C.

20. A catalytic system for the homo-, co- and ter-polymerization of olefin-unsaturated compounds which comprises:
(a) a catalyst supported on silica, prepared according to what is described in claim 1, having an atomic composition;

$$Si_{20-70}Mg_{0.5-10}Al_{0.2-1}Ti_1Cl_{5-40}.$$

(b) organo aluminum derivatives selected from aluminoxanes and compounds having general formula (V) $AlR_3$ wherein R is a $C_1$-$C_{20}$ alkyl group.

21. The catalytic system according to claim 20, wherein the molar ratio between aluminum of the organo aluminum derivatives (b) and titanium contained in (a) ranges from 5/1 to 2000/1.

22. The catalytic system according to claim 21, wherein the molar ratio between aluminum of the organo aluminum derivatives (b) and titanium contained in (a) ranges from 10/1 to 1000/1.

23. The catalytic system according to claim 22, wherein the molar ratio between aluminum of the organo aluminum derivatives (b) and titanium contained in (a) ranges from 20/1 to 800/1.

24. A process for the polymerization, copolymerization and terpolymerization of olefin-unsaturated compounds by means of the suspension method (slurry) in an inert diluent, or in a solution in inert solvents, at low, medium and high pressure and at temperatures ranging from 30 to 260° C.; characterized in that it is carried out in the presence of the catalytic system according to claim 20.

* * * * *